United States Patent [19]
Yoon et al.

[11] Patent Number: 5,948,020
[45] Date of Patent: Sep. 7, 1999

[54] IMPLANTABLE BIORESORBABLE MEMBRANE AND METHOD FOR THE PREPARATION THEREOF

[75] Inventors: Seok-Joon Yoon; Guw-Dong Yeo; You-Chan Kim; Min-Hyo Seo; Chaul-Min Pai, all of Daejeon; Jong-Pyoung Jung; Seung-Jin Lee, both of Seoul, all of Rep. of Korea

[73] Assignee: Sam Yang Co., Ltd., Seoul, Rep. of Korea

[21] Appl. No.: 08/765,021

[22] Filed: Dec. 26, 1997

[30] Foreign Application Priority Data

May 1, 1995 [KR] Rep. of Korea ............. 95-10672
Oct. 12, 1995 [KR] Rep. of Korea ............. 95-35025

[51] Int. Cl.$^6$ ...................................... A61F 2/02
[52] U.S. Cl. ................ 623/11; 600/37; 606/151; 606/152; 606/154
[58] Field of Search ................ 623/11; 600/37; 606/151, 152, 154

[56] References Cited

U.S. PATENT DOCUMENTS

| | | | |
|---|---|---|---|
| 3,463,158 | 8/1969 | Schmitt et al. | 606/151 |
| 3,526,228 | 9/1970 | Lyng | 606/151 |
| 5,084,051 | 1/1992 | Tormola et al. | 623/13 |
| 5,433,751 | 7/1995 | Christel et al. | 623/11 |
| 5,522,895 | 6/1996 | Mikos | 623/11 |
| 5,674,286 | 10/1997 | D'Alessio et al. | 623/11 |
| 5,735,863 | 4/1998 | Della Valle et al. | 606/152 |

*Primary Examiner*—Paul B. Prebilic
*Attorney, Agent, or Firm*—Anderson, Kill & Olick, P.C.

[57] ABSTRACT

An implantable bioresorbable membrane for the separation and regeneration of tissue in a defect site and augmentation of tissues surrounding other implants comprises: (a) porous bioresorbable polymer matrix made of a bioresorbable polymer selected from the group consisting of polylactic acid, poly(lactic-co-glycolic acid), polycarprolactone, polyparadioxanone, polytrimethylene carbonate and a mixture thereof; and (b) a reinforcing fabric made of bioresorbable fibers embedded in said matrix, and is produced by preparing a fabric as a support from bioresorbable fibrous materials, coating the fabric with a solution containing a bioresorbable polymer and a pore forming agent, and treating the coated fabric to generate pores.

9 Claims, 4 Drawing Sheets

IMPLANTABLE BIORESORBABLE MEMBRANE AND METHOD FOR THE PREPARATION THEREOF

This application is a national stage application under 37 CFR 1.371 of PCT/KR96/00063.

FIELD OF THE INVENTION

The present invention relates to an implantable bioresorbable membrane and a method for the preparation thereof, and more particularly to a bioresorbable membrane surgically inserted for the separation and regeneration of tissues at a defect site, for the augmentation of tissues surrounding other implants or for the controlled-release of a drug contained therein.

BACKGROUND OF THE INVENTION

A tissue when damaged or lost by a disease or injury does not usually recover fully to its original shape. For example, once an alveolar bone is eroded by a periodontal disease, the damaged alveolar bone and periodontal ligament tissue cannot be regenerated because of the excessive growth of connective tissues in the lost part of the bone tissue.

The tissue regeneration methods currently practiced to solve the above problem include a method of autografting and implanting a non-immunogenic animal or human bone, or an artificial bone substitute such as hydroxyapatite or tricalcium phosphate.

Another method which employs various membranes has also been developed to separate tissues at a defect site from the surrounding tissues and to induce regeneration of new tissues within the defect site.

International Patent Publication No. WO 90/11730 discloses a method for regenerating an alveolar bone by using, e.g., expanded polytetrafluoroethylene as a material for separating and reinforcing the alveolar bone tissue. However, in this method, non-degradable materials such as the expanded polytetrafluoroethylene must be removed by a secondary surgical operation, which may cause the infection or inflammation of the operated site.

Accordingly, various implantable articles of bioresorbable polymers have been developed to eliminate the need for secondary surgical operations.

International Patent Publication No. WO 92/10218 discloses a bioresorbable article for the separation and regeneration of tissues at a defect site, which comprises a fibrous material laminarly affixed to one surface of a barrier film. This articles is designed such that the regeneration of the desired tissues can take place in the space created on the fibrous side of the barrier film. The ingrowth of surrounding tissues into the defect site is prevented by keeping the surrounding tissues on the other side of the film.

However, the barrier film obstructs flows of material thereacross; particularly, timely integration of tissues from both sides of the film is hampered. Moreover, the space needed for the propagation of desired tissues can be secured by other means, e.g., by using an article which can be shaped to closely fit against surrounding tissues, thereby creating a space within the treatment site. To prepare such an article, a bioresorbable polymer having good malleability is required.

International Patent Publication No. WO 92/15340 discloses a bioresorbable polymer composition including a plasticizer, e.g., a citrate. The polymer composition is sufficiently malleable for fabricating therefrom an implantable article that is well adaptable to the shape of the treatment site to be covered. WO 92/15340 also specifies that said article should be made of a membrane having double layer structure consisting of a film having a fretted microstructure and another film having round micropores.

The disclosure by WO 92/15340 has a problem in that the plasticizer used in the claimed formulation may increase the risk of inflammation at the site of implantation.

A bioresorbable polymer membrane for use in the separation and regeneration of desired tissues should have a proper balance of the following properties depending on the desired effect of its intended use: (1) biodegradation in vivo, (2) structural or dimensional stability in vivo for a predetermined period, (3) malleability or flexibility, (4) tissue compatibility and adhesion, (5) cell-barrier property and (6) permeability of the extracellular fluid and other materials.

Many of the above properties appear to act counter to each other, e.g., a plasticizer which imparts good malleability may increase tissue inflammation, a fast rate of biodegradation would compromise the structural integrity, a membrane having a good cell-barrier property would also impede the permeabilities of other materials, and vise versa. The membrane of the present invention is advantageous in that: (1) it does not contain any plasticizer which may induce inflammation; (2) biocompatible polymers which are well-known in the art are employed; (3) its fiber matrix imparts good physical properties, e.g., tensile strength and structural stability to the membrane; (4) due to its highly porous structure it has a good flexibility and cell attachment; and (5) it becomes malleable when embossed.

SUMMARY OF THE INVENTION

Accordingly, it is a primary object of the present invention to provide an implantable bioresorbable membrane having a desirable balance of properties for the separation and regeneration of tissues damaged by a disease or injury.

Another object of the present invention is to provide a method for the preparation of the inventive implantable bioresorbable membrane.

In accordance with one aspect of the present invention, there is provided an implantable bioresorbable membrane comprising a woven or knitted fabric made of bioresorbable fibers as a support embedded in a bioresobable porous polymer matrix.

In accordance with another aspect of the present invention, there is provided a method for preparing an implantable bioresorbable membrane which comprises preparing a woven or knitted fabric as a support from bioresorbable fibrous materials, coating the fabric with a bioresorbable polymer solution and a pore-forming agent, drying and treating the coated fabric to obtain a bioresorbable membrane, and embossing the bioresorbable membrane.

BRIEF DESCRIPTION OF THE DRAWINGS

The above and other objects and features of the present invention will become apparent from the following description, taken in conjunction with the accompanying drawings, wherein.

DETAILED DESCRIPTION OF THE INVENTION

Figure 1:
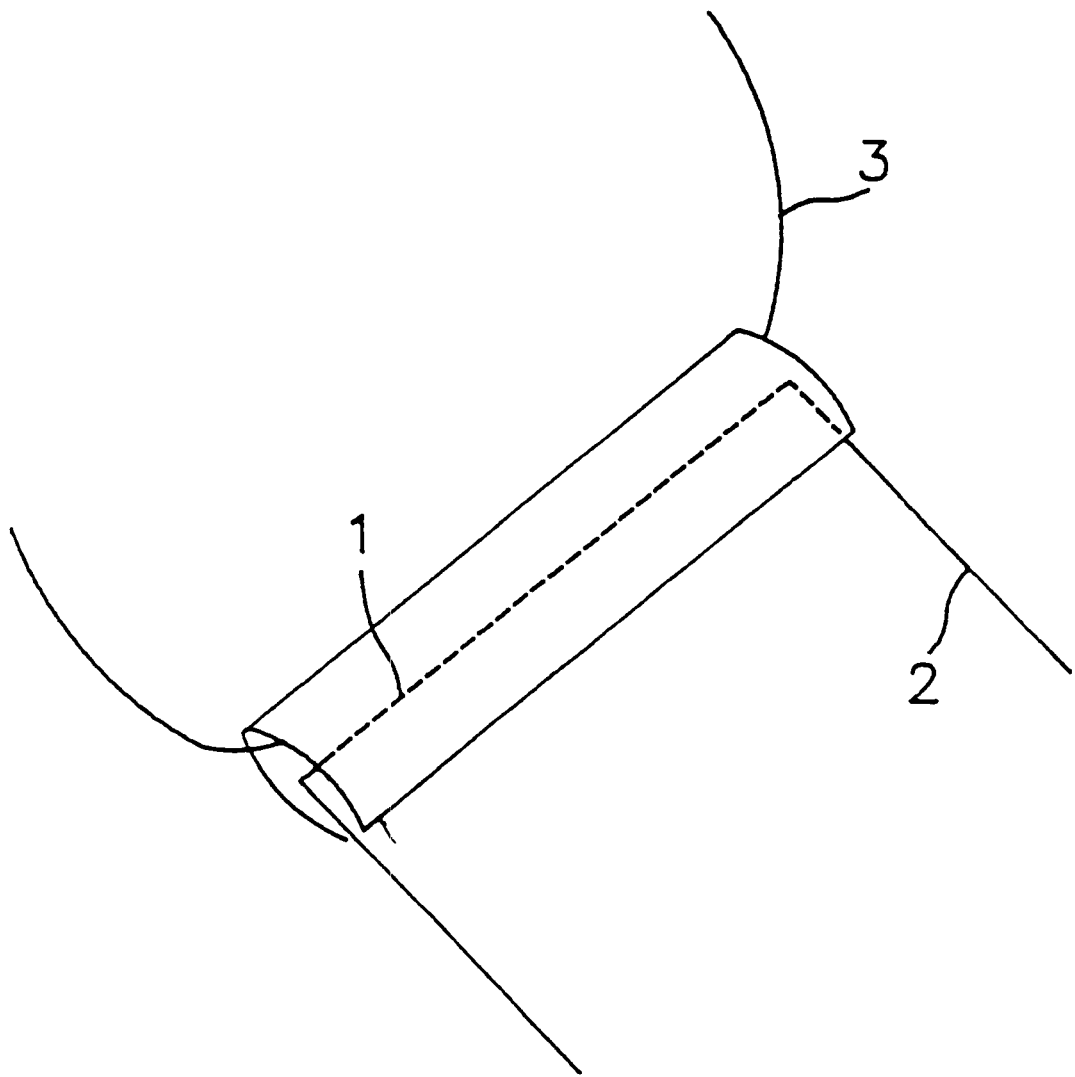
FIG. 1 is a schematic view showing the attachment of a suture to a bioresorbable implantable membrane prepared in accordance with the present invention.

The present invention provides an implantable bioresorbable membrane comprising a woven or knitted fabric made of bioresorbable fibers as a support embedded in bioresorbable/biocompatible porous polymer matrix.

The fabric employed as a support in the membrane of the present invention may be preferably made of a fibrous material conventionally known to be used as a suture in surgical operations, e.g., a monofilament fiber, multifilament fiber or a braided fiber thereof of polyglycolic acid, poly(lactic-co-glycolic acid) or polylactic acid, or the like, having a tensile strength of about 5.5 g/denier or more and having a fineness ranging from 35 to 150 denier. Preferred supporting fabric is a knitted or woven fabric having a fabric linear density of 20 to 100 ends/inch.

Although the bulk properties of polyglycolic acids or polylactic acids are characterized by a low plasticity and flexibility, a fabric prepared therefrom in the form of woven or knitted fabric has a good flexibility and tensile strength. A polyglycolic acid fabric is particularly preferred due to its high tensile strength and fast degradation rate for the intended use in the present invention.

The woven or knitted fabric of the present invention is coated with a solution containing a bioresorbable polymer (hereinafter referred to as a coating solution) to form a polymer membrane thereon. A co-solvent system comprising a primary solvent and a secondary solvent is used in preparing the coating solution. Microporous structure in the polymer matrix is created by phase-inversion caused by the difference in solubility of the polymer between the primary solvent and the secondary solvent. The coating solution may be prepared simply by dissolving a biodegradable polymer in a primary solvent and adding thereto a secondary solvent. The coating solution may further comprise a pore-forming agent(porogen) which is later removed by a suitable extraction treatment to make the matrix porous. Water-soluble particles may be suitably used as the porogen.

Representative bioresorbable polymers which may be employed in the coating solution of the present invention are selected from the group consisting of polylactic acid, poly(latic-co-glycolic acid), polycaprolactone, polyparadioxanone, polytrimethylene carbonate and the like. Poly-D,L-lactic acid, poly(L-lactic-co-glycolic acid) poly(D,L-lactic-co-glycolic acid), acid and polycaprolactone may be preferably employed alone or in a combination thereof. The degradation rates of the biodegradable materials thereof may be controlled by adjusting the molecular weight, the degree of crystallization, the amount and kind of additives, among others.

The primary solvent which may be employed in preparing the coating solution is preferably methylene chloride. Representative of the secondary solvent may include ethanol, N-methyl pyrrolidone and ethyl acetate, and a mixture thereof.

Optionally, porogen which can be removed in a later solvent treatment step may be employed in the coating solution for the purpose of generating micropores in the coated film. Examples of porogen which may be used in the present invention include water-soluble particles such as salts, e.g., sodium chloride, potassium chloride, calcium chloride, ammonium chloride, sodium carbonate, sodium bicarbonate, sodium citrate and the like; saccharides, e.g., fructose, maltose, dextran, pectin, xylan, alginate, carrageenan and the like; and polyvinylpyrrolidone.

The bioresorbable membrane of the present invention may be prepared by coating a woven or knitted fabric with a coating solution optionally containing the above-mentioned porogen to produce a membrane having channels formed by interconnecting micropores.

When the one of the porogens mentioned above is employed, the membrane may be prepared by: preparing a porogen having a desirable particle size by way of using a spray dryer or a mill; adding the porogen to a polymer solution; coating the resultant mixture onto the fabric; drying the coated fabric to remove solvent; washing the dried fabric with water or other suitable solvent to remove the porogen embedded in the membrane; and drying the fabric to produce a porous membrane having micropores of substantially the same size as that of the porogen.

The bioresorbable membrane of the present invention has interconnected micropores, forming open channels across the membrane. Thus, it enables an exchange of materials, e.g., extracellular fluid containing oxygen and other nutrients, between the tissues of both sides of the membrane. This feature is important in understanding why the membrane of the present invention is particularly effective in healing and adhesion of the tissue at a defect site.

Also, the highly porous membrane of the present invention has an excellent ability of tissue attachment, which further enhances the regeneration of damaged tissues as well as the integration of the surrounding tissues to the barrier membrane.

The biodegradable material used in the present invention tends to have a low wettability in water due to the hydrophobic nature of the polymer used. To further improve the wettability, the porous membrane prepared in accordance with the present invention is preferably embossed by pressing the membrane onto an embossing plate heated to a temperature over the glass transition temperature(Tg). This embossing treatment not only enhances the permeation of water and water-soluble materials but it also improves the stiffness and malleability of the inventive membrane, thereby making it possible to closely match the membrane to the shape of the treatment site and to secure a space for the regeneration of desired tissues.

A typical biodegradable polymer has a low flexibility at room temperature due to a glass transition temperature of 45° C. or higher. To solve the flexibility problem, International Patent Publication No. WO 92/15340 discloses a method of adding a plasticizer, e.g., various citric acid ester, or ethyl terminated oligomers of lactic acid. However, the plasticizer used in the above disclosure may include inflammation at the implanted site. Further, U.S. Pat. No. 5,250, 584 discloses copolymers of lactide/glycolide and lactide/caprolactone which are flexible at room temperature. However, the improved flexibility at room temperature of the claimed copolymers may compromise the dimensional stability of a membrane made thereof.

In order to avoid the problems associated with the prior art references mentioned above, the present invention provides a new method comprising an embossing treatment step, which improves both the malleability and dimensional stability of a porous bioresorbable membrane. The embossing treatment of the present invention thus avoids the use of a plasticizer which may cause an undesirable side effect, and at the same time, imparts a combination of desirable properties, i.e., good malleability, dimensional stability, and permeability of water or water-soluble materials, to a porous bioresorbable membrane.

A biodegradable suture may be preferably attached to the membrane of the present invention for the convenience of operation. For example, a method illustrated in FIG. 1 may be employed when the membrane of the present invention is to be introduced for the regeneration of a damaged alveolar one. In FIG. 1, the membrane of the present invention(2) is bound firmly to the root of a tooth through the use of a suture(3) and an added porous film(1). Such method may restrain the mobility of the membrane and enables the epithelial cells to grow and attach to the boundary part of the tooth root and membrane.

The membrane of the present invention may further comprise drugs for the purpose of the prevention of infection and inflammation, stimulation of tissue regeneration in the inserted site and the like. Representative of the drugs which may be incorporated in the membrane include antiphlogistic such as flubiprofen, ibuprofen, indomethacin, naproxen, mefenamic acid and the like; antibiotics such as tetracycline, minocycline, oxytetracycline and the like; metronidazole; a platelet-derived growth factor; an insulin-like growth factor; an epithelial growth factor; a tumor proliferative factor; bone morphogenetic protein; and a mixture thereof.

The following examples are intended to further illustrate the present invention, without limiting its scope.

Reference 1: In Vitro Cell Attachment of the Membrane

The number of cells attached to a polymer membrane was measured as follows: each polymer or a mixture of polymers shown in Table 1 was dissolved in methylene chloride, the resultant solution was cast and dried to produce a film having a thickness of about 100 $\mu$m. The film was spread on the bottom of a petridish and fibroblasts derived from the dermal layer of a rat were placed thereon with a culture medium. Finally, the number of cells attached to the polymer membrane was counted, and the results are shown in Table 1.

TABLE 1

| Polymer Composition | No. of Attached Cells** | |
|---|---|---|
| | After 1 day | After 3 days |
| A (iv* 0.8) | 92500 | 177500 |
| A (iv 1.4) | 82200 | 186300 |
| B (iv 0.7) | 89700 | 173500 |
| B (iv 1.4) | 105400 | 220000 |
| C (iv 0.8) | 105000 | 242500 |
| C (iv 1.2) | 112500 | 275000 |
| D (iv 0.4) | 61200 | 159000 |
| E (iv 3.9) | 53000 | 161300 |
| E (iv 6.3) | 49400 | 148900 |
| 90 wt % A (iv 0.8)/10 wt % E (iv 6.3) | 87200 | 189000 |
| 70 wt % A (iv 0.8)/30 wt % E (iv 6.3) | 81700 | 164000 |
| 90 wt % B (iv 1.4)/10 wt % E (iv 3.9) | 88900 | 194100 |
| 70 wt % B (iv 1.4)/30 wt % E (iv 3.9) | 83700 | 178800 |

Footnote:
A: poly-L-lactic-glycolic acid (75:25)
B: poly-D,L-lactic-glycolic-acid (55:45)
C: poly-D,L-lactic acid
D: polycaprolactone
E: poly-L-lactic acid
*iv menas intrinsic viscosity.
**170,000 fibroblasts was placed on each treatment.

As shown in Table 1, poly-D,L-lactic acid, poly(L-lactic-co-glycolic acid) poly(D,L-lactic-co-glycolic acid) and with a relatively low molecular weight and crystallization degree generally have an excellent property for cell attachment. Further, the cell attachment of poly-L-lactic acid does not deteriorate when mixed with poly(lactic-co-glycolic acid) at a ratio of 1:9 to 4:6. Therefore, a mixture of these polymers may be used in fabricating an implantable membrane.

Reference 2: In Vitro Swelling of Membranes by Hydrolysis

To examine the rate of swelling by hydrolysis of the biodegradable polymer materials, polymer materials of various compositions shown in Table 2 were dissolved in methylene chloride, cast and dried to produce films of a 100 $\mu$m thickness. Each of these films was put in a stirred phosphate buffered saline (PBS)(pH 7.4, 37° C.) and sampled twice after 1 and 3 days to determine the changes in the thickness of the film. The results are shown in Table 2.

TABLE 2

| Polymer Composition | Change in Thickness (%) | |
|---|---|---|
| | After 1 day | After 3 days |
| A (iv 0.8) | 16.6 | 25.6 |
| A (iv 1.4) | 11.7 | 22.3 |
| B (iv 0.7) | 6.7 | 18.9 |
| B (iv 1.4) | 5.4 | 17.0 |
| C (iv 0.8) | 23.8 | 36.5 |
| C (iv 1.2) | 14.4 | 32.4 |
| D (iv 0.4) | 11.2 | 21.9 |
| E (iv 3.9) | 3.4 | 8.5 |
| E (iv 6.3) | 3.1 | 9.5 |
| 70 wt % A (iv 0.8)/30 wt % E (iv 6.3) | 6.9 | 10.1 |
| 70 wt % B (iv 1.4)/30 wt % E (iv 3.9) | 7.8 | 9.8 |

Footnote:
A: poly-L-lactic glycolic acid (75:25)
B: poly-D,L-lactic glycolic acid (55:45)
C: poly-D,L-lactic acid
D: polycaprolactone
E: poly-L-lactic acid As shown in Table 2, the film made of poly-D,L-lactic acid, which exhibited the highest cell attachment, shows the highest swelling rate. The films of poly(L-lactic-co-glycolic acid) acid, and poly(D,L-lactic-co-glycolic acid) also show large changes in thickness while the film of poly-L-lactic acid swells slowly. A significant decrease in the swelling rate was observed when the film of poly(lactic-co-glycolic acid) contained poly-L-lactic acid.

Reference 3: Physical Properties of a Membrane in Relation with its Porous Structure and Embossing Treatment In order to examine the property changes brought about by the formation of micropores in a membrane and also by an embossing treatment, a non-porous membrane, a porous membrane, and an embossed porous membrane were prepared, and stiffness and malleability thereof were measured as follows.

1.6 g of poly(L-lactic-co-glycolic acid) (iv 0.8) and 0.4 g of poly-L-lactic acid (iv 6.3) were dissolved in 25 ml of methylene chloride, and the resultant solution was casted and dried to produce a film of 200 $\mu$m thickness. The film thus obtained was dried in a vacuum oven for one day to remove residual solvent to produce a non-porous membrane.

1.6 g of poly(L-lactic-co-glycolic acid) (iv 0.8) and 0.4 g of poly-L-lactic acid (iv 6.3) were dissolved in 25 ml of methylene chloride, and 20 g of sodium citrate in the form of a fine powder was added thereto. After the resultant mixture was dispersed homogeneously, it was cast and dried to produce a film of 200 μm thickness. The film was dried in a vacuum oven for one day to remove residual solvent, stirred in a water tank for 6 hours in order to extract sodium citrate and dried to obtain a porous membrane.

Further, the same procedure as described above was repeated except that an additional embossing treatment of the porous membrane was conducted by pressing the membrane onto a plate having 20 protrusion/cm² preheated to 150° C., to produce an embossed porous membrane.

Figure 2:
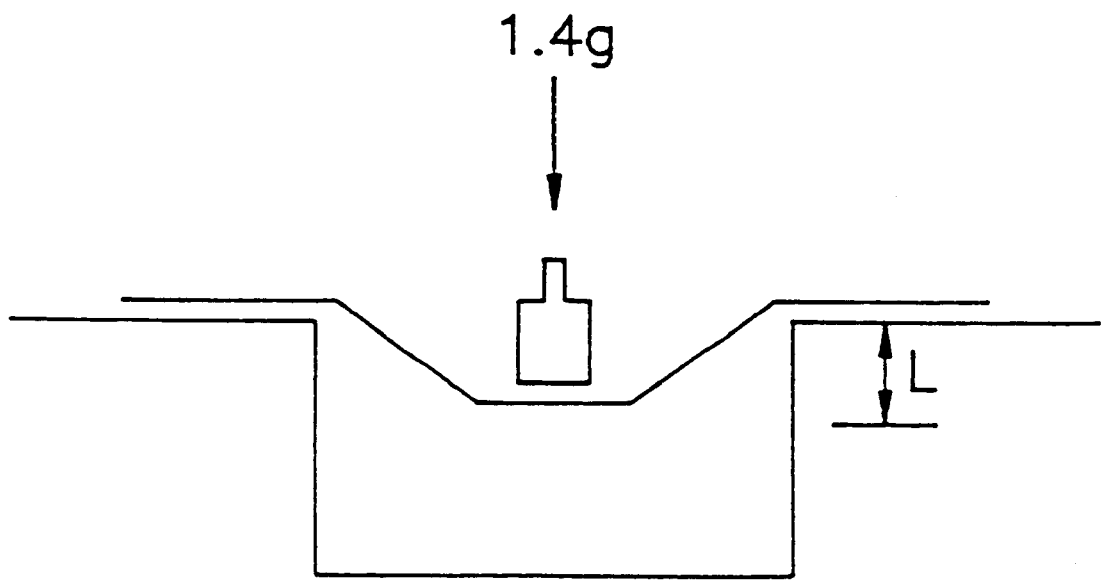
FIG. 2 shows a schematic view of an apparatus for measuring the stiffness of a membrane.

Each of membranes thus prepared was cut to obtain a 12 mm×60 mm test piece, which was placed on the equipment illustrated in FIG. 2. The stiffness of each membrane was measured by putting a 1.4 g weight on the membrane piece, and determining the oppressed depth (L).

Figure 3:
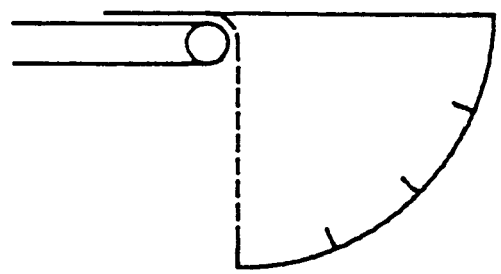
FIG. 3 presents a schematic view of an apparatus for measuring the malleability of a membrane.

The malleability of a membrane was estimated by bending a membrane sample by 90° using the equipment illustrated in FIG. 3, releasing the sample and measuring the degree of the bent angle after 10 seconds. The results of such stiffness and malleability measurements are shown in Table 3.

TABLE 3

|  | A | B | C |
|---|---|---|---|
| Stiffness | 1 | 16 | 1 |
| Malleability(°) | 0 | 23 | 34 |

Footnote:
A: non-porous membrane
B: porous membrane
C: embossed porous membrane

Table 3 shows that the porous membrane B has a higher malleability than the non-porous membrane, although its stiffness is low. The embossed porous membrane exhibits both an improved stiffness and malleability.

EXAMPLE 1

A knitted fabric with a fabric linear density of 45 ends/inch was produced by knitting polyglycolic acid multifilament having a fineness of 75 denier.

Subsequently, 0.3 g of poly-L-lactic acid and 1.7 g of poly(L-lactic-co-glycolic acid) were dissolved in 30 ml of methylene chloride; and 22 g of sodium citrate in the form of a fine powder was added thereto and dispersed with mechanical stirring to produce a polymer coating solution.

The polymer coating solution thus prepared was spreaded onto the knitted polyglycolic acid fabric prepared above. The coated fabric was dried to remove residual solvent, and put in a water tank in order to extract sodium citrate to produce a porous membrane.

Figure 4:
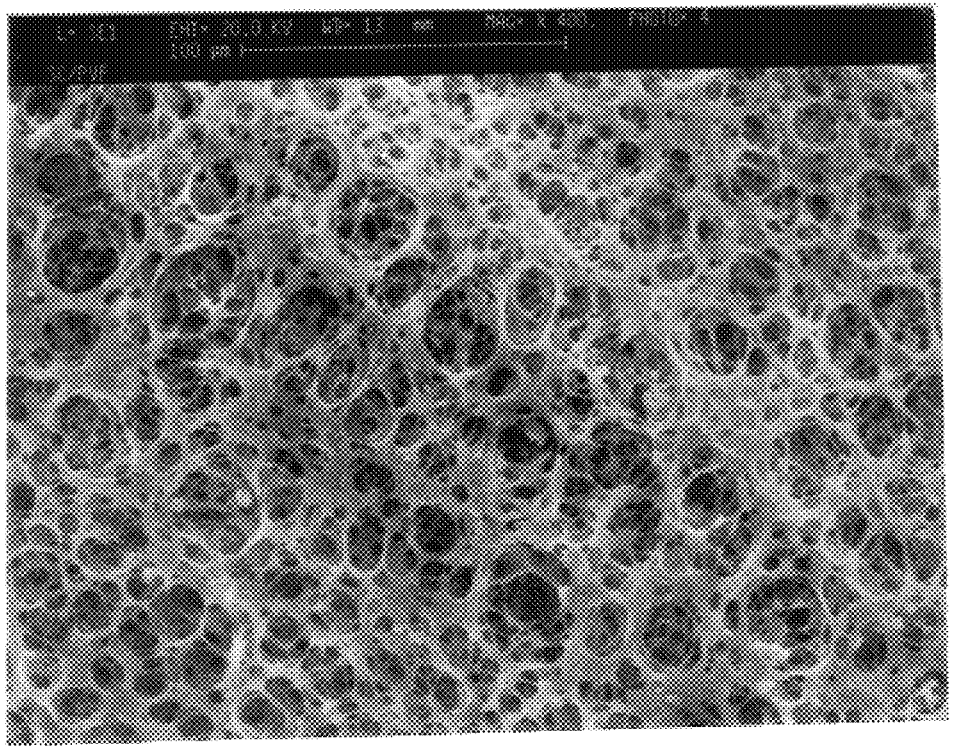
FIG. 4 reproduces a scanning electron microscope (SEM) photograph (400 magnifications) of a bioresorbable implantable membrane prepared in accordance with an embodiment of the present invention.

The micropores of the membrane thus obtained were observed with a scanning electron microscope (SEM). Reproduced in FIG. 4 is an SEM photograph (400 magnifications) of the above membrane. Numerous micropores of 100 μm or less in diameter are observed and these are interconnected to form channels across the membrane.

The above membrane was cut to 5 mm×60 mm sample pieces and put in a stirred PBS (pH 7.4, 37° C.). The samples were taken out at 2 week intervals and the tensile strength and elongation were measured. The changes in the physical properties with time are shown in Table 4.

TABLE 4

|  | Time (week) | | | | |
|---|---|---|---|---|---|
|  | 0 | 2 | 4 | 6 | 8 |
| Tensile Strength (kg) | 0.92 | 0.65 | 0.58 | 0.45 | 0.43 |
| Elongation (%) | 47.40 | 30.60 | 14.58 | 9.78 | 5.10 |

From the above results, it can be seen that the membrane prepared in accordance with the present invention maintains an adequately high strength during a sufficient period of time. Accordingly, a sudden destruction of the membrane at the time of operation or in early stages of implantation is not expected to occur.

EXAMPLE 2

A knitted fabric with a fabric linear density of 45 ends/inch was produced by knitting polyglycolic acid multifilament having a fineness of 75 denier.

Subsequently, 0.3 g of poly-L-lactic acid and 1.7 g of poly(L-lactic-co-glycolic acid) were dissolved in 30 ml of methylene chloride, and 10 ml of ethyl acetate and 0.8 g of polyvinyl pyrrolidone were added thereto and stirred to produce a polymer coating solution.

This polymer coating solution was spreaded onto the knitted fabric obtained above, and the coated fabric was dried to remove residual solvent and put in a stirred water tank to extract out residual polyvinylpyrrolidone to produce a porous membrane.

Figure 5:
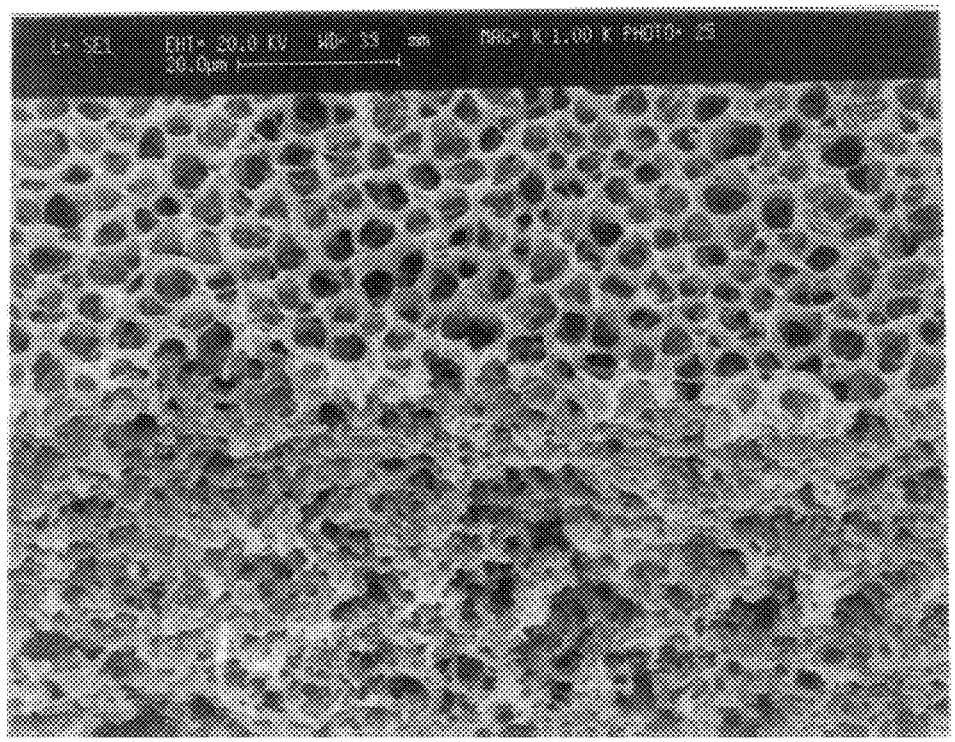
FIG. 5 is an SEM photograph (1000 magnifications) of a bioresorbable implantable membrane prepared in accordance with another embodiment of the present invention.

The micropores of the membrane thus obtained were observed with SEM. FIG. 5 is an SEM photograph (1000 magnifications) of the membrane. It can be shown that very homogeneous micropores of less than 10 μm in diameter exist on the surface of the membrane and that most of these micropores are interconnected to form channels across the membrane.

EXAMPLE 3

2 of poly(L-lactic-co-glycolic acid) was dissolved in 25 ml of methylene chloride, and thereto was added 20 g of sodium citrate in the form of a fine powder. The resulting mixture was homogenized, cast and dried to produce a film of 200 μm thickness. The film was dried in a vacuum oven for one day to remove residual solvent, stirred in a water tank for 6 hours to extract out sodium citrate, and dried again to produce a porous membrane. Then, an embossing treatment was conducted by pressing the above membrane onto a plate with 20 protrusion/cm² at 150° C. to produce an embossed porous membrane.

The transferability of the membrane before/after the embossing treatment was measured by introducing the membrane in the Frantz cell measuring the amount of transferred bovine serum albumin with time. The results are shown in Table 5.

TABLE 5

|  | Amount Transferred (μg/ml) | |
|---|---|---|
| Time (hr) | Before embossing | After embossing |
| 0 | 0 | 0 |
| 1 | 28.5 | 104.8 |

TABLE 5-continued

| | Amount Transferred (μg/ml) | |
|---|---|---|
| Time (hr) | Before embossing | After embossing |
| 3 | 107.0 | 256.0 |
| 5 | 186.2 | 304.0 |
| 7 | 279.1 | 349.0 |
| 24 | 408.3 | 491.4 |

As shown in Table 5, the transfer rate is initially slow in case of the non-embossed membrane, whereas the embossed membrane allows a relative steady, high transfer rate of the aqueous solution.

EXAMPLE 4

A knitted fabric with a fabric linear density of 45 ends/inch was produced by knitting polyglycolic acid multifilament having a fineness of 50 to 110 denier.

Subsequently, 0.3 g of poly-L-lactic acid and 1.7 g of poly(L-lactic-co-glycolic acid) were dissolved in 30 ml of methylene chloride. 10 ml of ethyl acetate and 0.2 g of tetracycline were added thereto and homogenized.

The resulting solution was spreaded onto the knitted fabric of polyglycolic acid prepared above, and the coated fabric was dried to remove residual solvent to produce a porous membrane containing a drug.

The above membrane was placed in a stirred PBS (pH 7.4, 37° C.); and sampled at regular intervals. The amount of tetracycline released was quantified using a UV spectrophotometer.

Figure 6:
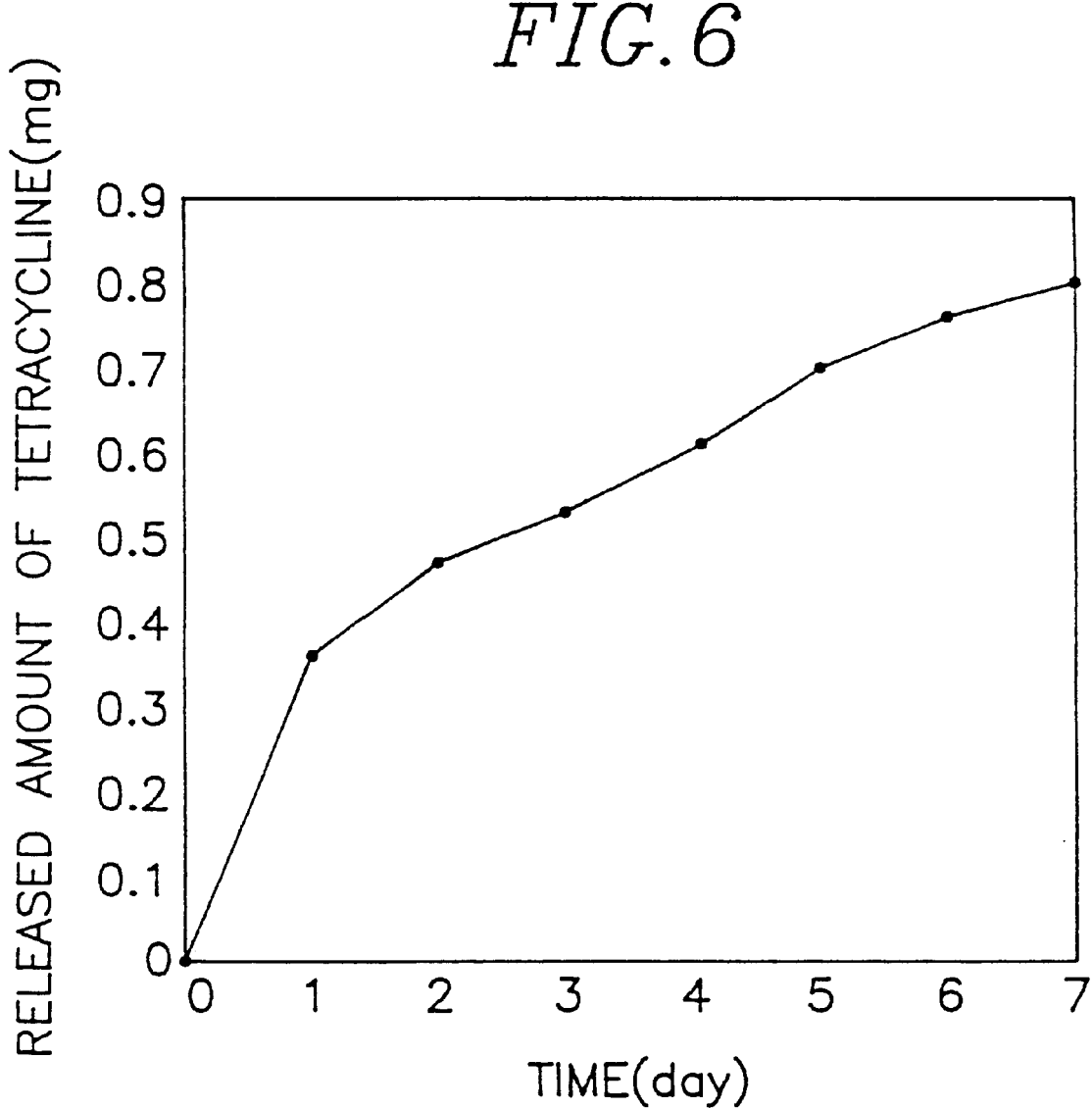
FIG. 6 plots the amount of tetracycline released from the inventive membrane containing tetracycline(TC) with time.

FIG. 6 is a graph showing the time-dependent change in the amount of tetracycline released from the membrane. The tendency of an initially fast release of the tetracycline is evident, which suggests that the risk of infection or inflammation in the early stage of implantation of the membrane can be effectively controlled.

As shown in the above examples, a porous membrane of the present invention has an excellent malleability and improved strength, which makes it possible to closely fit the membrane to the shape of the region to be covered, and also to maintain the shape during a prescribed period after implantation.

Further, in accordance with the present invention, the growth of desired tissues in the treatment site is not impeded because of the relatively facile material transport through the microporous channels. Further, the stiffness and malleability of the membrane of the present invention can be improved by an embossing treatment.

Accordingly, the embossed porous membrane prepared in accordance with the present invention may be used for guided tissue regeneration, tissue supporting and covering, maintenance and support of artificial organ inserted into body, and as a drug carrier, and the like.

While the invention has been described with respect to the specific embodiments, it should be recognized that various modifications and changes may be made by those skilled in the art to the invention which also fall within the scope of the invention as defined by the appended claims.

What is claimed is:

1. An implantable bioresorbable membrane for the separation and regeneration of tissue in a defect site and the augmentation of tissues surrounding other implants, having a high tensile strength, good malleability and dimensional stability comprising:

(a) a porous bioresorbable polymer matrix made of a bioresorbable polymer selected from the group consisting of polylactic acid, poly(lactic-co-glycolic acid), polycarprolactone, polyparadioxanone, polytrimethylene carbonate and a mixture thereof; and (b) a reinforcing fabric made of bioresorbable fibers embedded in said matrix, wherein interconnecting micropores are distributed through the thickness of said matrix so as to allow the permeation of nutrients therethrough and to enhance the tissue attachment thereto.

2. The implantable bioresorbable membrane of claim 1 wherein the bioresorbable fibers are monofilaments, multifilaments, or braided forms thereof made of a polymer selected from the group consisting of polyglycolic acid, poly(lactic-co-glycolic acid)and polylactic acid.

3. The implantable bioresorbable membrane of claim 1 wherein the bioresorbable fibers are monofilaments, multifilaments, or braided forms thereof made of polyglycolic acid.

4. The implantable bioresorbable membrane of claim 1 wherein the porous bioresorbable polymer matrix has micropores of less than 100 μm in diameter.

5. The implantable bioresorbable membrane of claim 1 further comprising an additive dispersed in said matrix, the additive being selected from the group consisting of flubiprofen, ibuprofen, indomethacin, naproxen, mefenamic acid, tetracycline, minocycline, oxytetracycline, metronidazole, a platelet-derived growth factor, an insulin-like growth factor, an epithelial growth factor, a tumor proliferative factor, bone morphogenetic protein, and a mixture thereof.

6. The implantable bioresorbable membrane of claim 1 wherein a second bioresorbable fiber is attached to the membrane as a suture.

7. A method for preparing an implantable bioresorbable membrane which comprises preparing a fabric as a support from bioresorbable fibrous materials, coating the fabric with a solution containing a bioresorbable polymer selected from the group consisting of polylactic acid, poly(lactic-co-glycolic acid), polycaprolactone, polyparadioxanone, polytrimethylene carbonate and a mixture thereof, drying the coated fabric, and embossing the coated fabric.

8. The method of claim 7 wherein the bioresorbable polymer solution comprises methylene chloride and a second solvent, the second solvent being ethanol, N-methylpyrrolidone or ethyl acetate or a mixture thereof.

9. The process of claim 7 wherein the bioresorbable polymer solution contains water-soluble particles of a compound selected from the group consisting of sodium chloride, potassium chloride, calcium chloride, ammonium chloride, sodium carbonate, sodium bicarbonate, sodium citrate, fructose, maltose, dextran, pectin, xylan, alginate, carrageenan, polyvinylpyrrolidone and a mixture thereof as a micropore formation additive, which further comprises the steps of removing the particles by extracting the dried, coated fabric with water, or with a suitable aqueous solution, to obtain a porous membrane and drying the porous membrane.

* * * * *

UNITED STATES PATENT AND TRADEMARK OFFICE
CERTIFICATE OF CORRECTION

PATENT NO. : 5,948,020   Page 1 of 1
DATED : September 7, 1999
INVENTOR(S) : Seok-Joon Yoon, et al.

It is certified that error appears in the above-identified patent and that said Letters Patent is hereby corrected as shown below:

PCT Filed: May 1, 1996
PCT No.:PCT/KR96/0063
§ 371 Date: December 26, 1996
§ 102(e) Date: December 26, 1996
PCT Pub. No.: WO 96/34634
PCT Pub. Date: November 7, 1996

Signed and Sealed this

Twenty-eighth Day of August, 2001

*Attest:*

*Attesting Officer*

NICHOLAS P. GODICI
*Acting Director of the United States Patent and Trademark Office*